(12) United States Patent
Mori et al.

(10) Patent No.: US 7,833,792 B2
(45) Date of Patent: Nov. 16, 2010

(54) TEST STRIP MEASURING METHOD

(75) Inventors: Masaaki Mori, Hirakata (JP); Masao Ninomiya, Hirakata (JP); Tomokuni Inoue, Hirakata (JP); Eiji Ikegami, Kyoto (JP); Akira Tanaka, Hirakata (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1016 days.

(21) Appl. No.: 11/119,704

(22) Filed: May 3, 2005

(65) Prior Publication Data

US 2005/0191210 A1    Sep. 1, 2005

Related U.S. Application Data

(62) Division of application No. 10/181,490, filed as application No. PCT/JP01/00606 on Jan. 30, 2001, now abandoned.

(30) Foreign Application Priority Data

| Feb. 2, 2000 | (JP) | ............................. 2000-024938 |
| Feb. 2, 2000 | (JP) | ............................. 2000-024939 |
| May 30, 2000 | (JP) | ............................. 2000-160646 |

(51) Int. Cl.
*G01N 33/48* (2006.01)

(52) U.S. Cl. ............................. 436/50; 436/46; 422/66; 422/67

(58) Field of Classification Search ............... 436/46, 436/50; 422/66, 67
See application file for complete search history.

(56) References Cited

U.S. PATENT DOCUMENTS

| 3,980,437 | A | 9/1976 | Kishimoto et al. |
| 4,302,420 | A | 11/1981 | Jakubowicz et al. |
| 5,728,352 | A | 3/1998 | Poto et al. |
| 5,945,341 | A | 8/1999 | Howard, III |
| 5,985,675 | A | 11/1999 | Charm et al. |

FOREIGN PATENT DOCUMENTS

| DE | 26 26 600 B1 | 7/1977 |
| EP | 0 383 209 A1 | 8/1990 |
| EP | 0 837 320 A2 | 4/1998 |
| JP | 03-095431 | 4/1991 |
| JP | 03-095435 | 4/1991 |
| JP | 07-005110 | 1/1995 |
| JP | 11-142338 | 5/1999 |
| WO | WO 9607907 A1 | 3/1996 |

*Primary Examiner*—Lyle A Alexander
(74) *Attorney, Agent, or Firm*—Finnegan, Henderson, Farabow, Garrett & Dunner L.L.P.

(57) ABSTRACT

In a test strip measuring method in which a coloration measurement is conducted while a test strip (4) is being moved, there are detected the optical characteristics R of the ground of a test strip and the optical characteristics T of a test line (4*b*) which has appeared on the test strip, and the test strip is judged based on the difference or ratio between R and T. Even though the ground of the test strip presents variations in optical characteristics, and even though there are variations among samples or among test strips, such variations can be absorbed, thus assuring an accurate judgment.

17 Claims, 16 Drawing Sheets

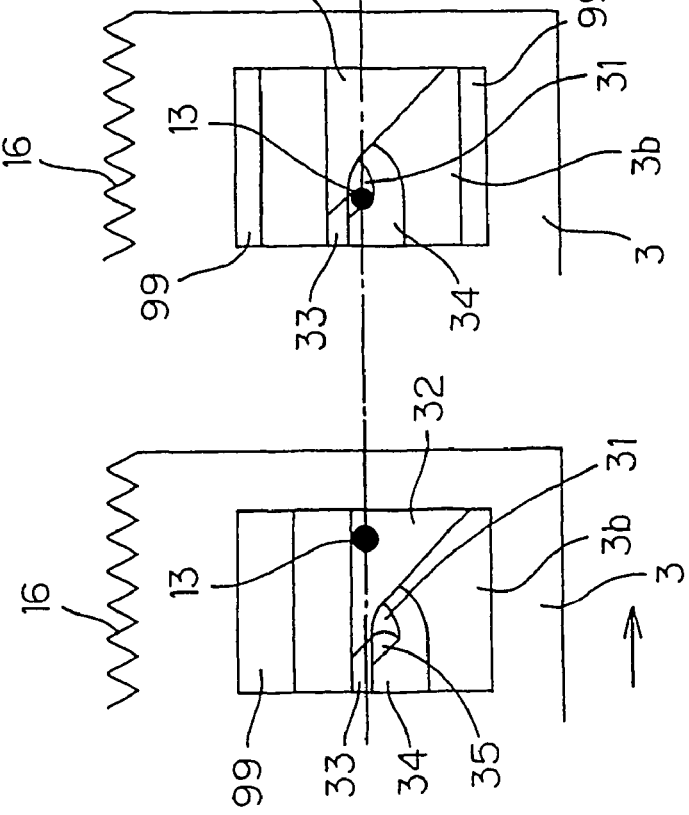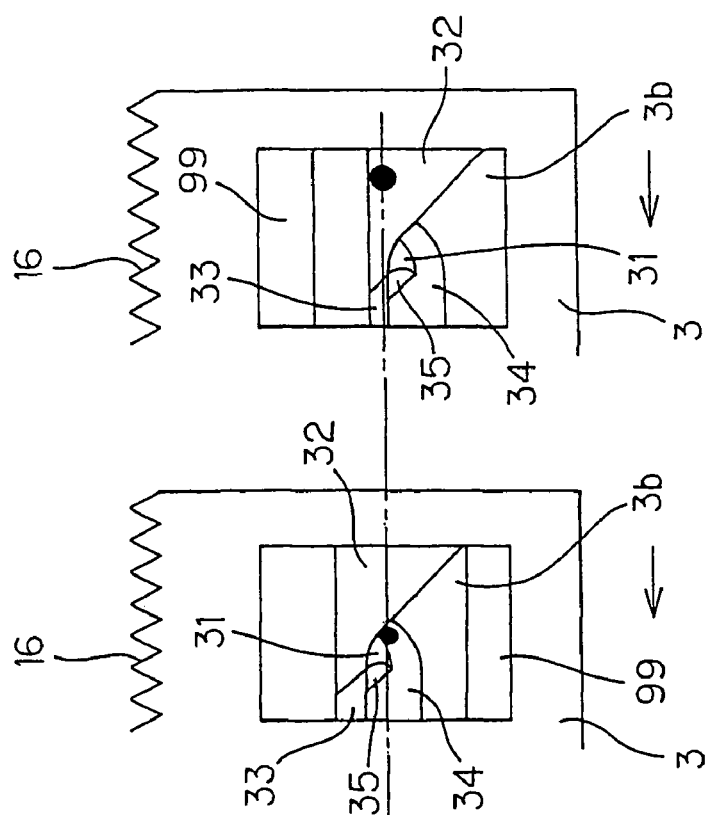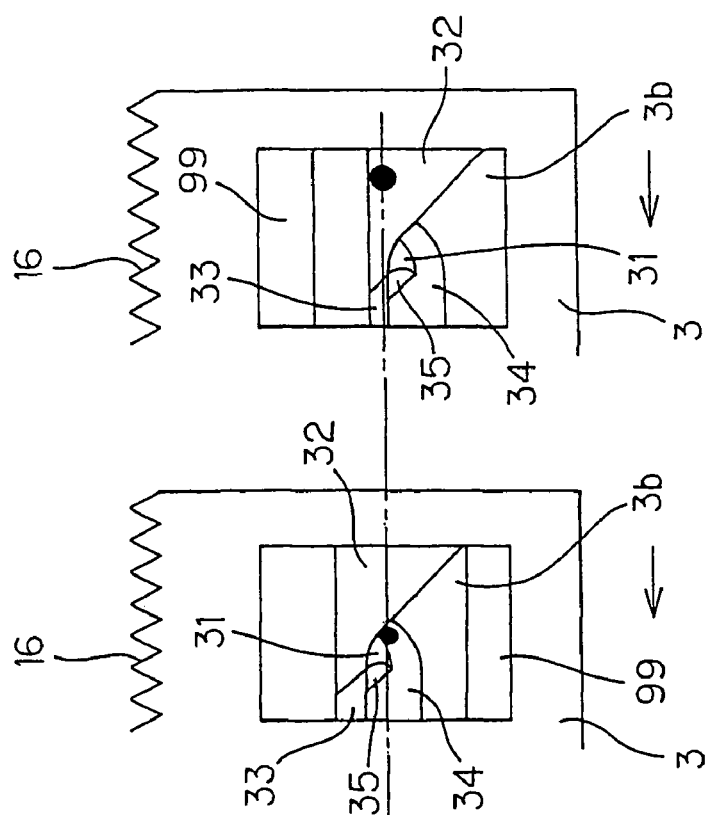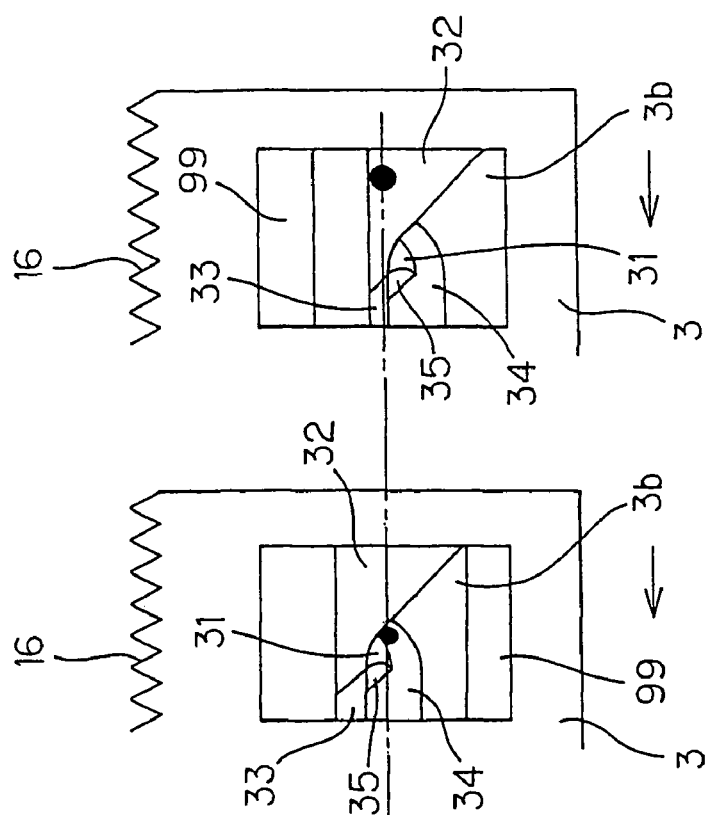

TEST STRIP MEASURING METHOD

This application is a divisional of U.S. application Ser. No. 10/181,490 filed Jul. 19, 2002, now abandoned, which is a §371 of PCT/JP01/00606, filed Jan. 30, 2001, all of which are incorporated herein by reference.

BACKGROUND OF THE INVENTION

1. Field of the Invention

The present invention relates to test strip measuring method and device in which measurement is conducted while a test strip is being moved.

2. Description of Related Art

There is known a test strip measuring method in which a test strip is immersed in a liquid such as urine, blood, saliva or the like and the resultant coloration is measured to automatically judge whether the specimen is positive or negative.

A. Examples of the test strip measuring method of the type above-mentioned, include a method of detecting, while a test strip is being moved, the optical characteristics T (e.g., reflective intensity) of a test line which has appeared on the test strip.

However, the optical characteristics of the grounds of different test strips vary from one another. This involves the likelihood that with the mere use of the optical characteristics T of the test line which has appeared on the test strip, no accurate measurement can be achieved, resulting in erroneous judgment.

Further, there are instances where test strip measuring devices are different in test-strip moving speed from one another, failing to accurately identify a test line.

In view of the foregoing, it is an object of the present invention to provide, in a test strip measuring method of measuring the coloration of a test strip while the same is being moved, a test strip measuring method capable of achieving an accurate quantitative measurement or qualitative judgment with variations in the optical characteristics of the grounds of different test strips taken into consideration.

It is a further object of the present invention to provide a test strip measuring method capable of achieving an accurate quantitative measurement or qualitative judgment even though test strip measuring devices are different in test-strip moving speed from one another.

B. Examples of the test strip measuring device above-mentioned include a device arranged to conduct measurement while a test strip is being moved. As a mechanism for moving the test strip, there is used a rack pinion mechanism or the like for changing the rotation of a motor to a linear motion.

However, the use of a mechanism using a motor causes the test strip measuring device to be increased in size, weight and power consumption. Thus, a compact mechanism requiring less power consumption has been long desired.

In view of the foregoing, it is another object of the present invention to provide, in a test strip measuring device for measuring the coloration of a test strip while the same is being moved, a test strip measuring device capable of moving a test strip with a simple arrangement.

SUMMARY OF THE INVENTION

In this specification, "qualitative judgment" refers to make a judgment of negativity or positivity, while "quantitative measurement" refers to obtain a determinant DET in the form of a numerical value.

According to the present invention, a test strip measuring method comprises the steps of: detecting the optical characteristics R of the ground of a test strip; detecting the optical characteristics T of a test line which has appeared on the test strip; and conducting a quantitative measurement or a qualitative judgment on the test strip based on the difference or ratio between R and T.

Here, the term of "optical characteristics" refers to reflective intensity, transmission intensity, fluorescence intensity and the like.

According to this method, even though the grounds of different test strips present variations in optical characteristics, such variations can be absorbed, thus assuring an accurate quantitative measurement or qualitative judgment.

The present invention may be arranged such that there is estimated the point of time when the test line will appear after the test strip has started moving, or the position where the test line will appear, and a judgment of negativity is made when the test line did not appear at the estimated point of time or in the estimated position. In such an arrangement, it is possible to prevent a portion which is not actually the test line, from being erroneously detected as the test line.

The present invention may be arranged such that there is measured a period of time T1 from the start of test strip movement to the point of time when the forefront end of the test strip in the moving direction, has been detected, and there can be estimated, based on the period of time T1, a period of time after which the test line will appear. When the period of time T1 is used as a basis, a period of time after which the test line will appear, can accurately be estimated or determined even though test strip holders are different in moving speed from one another.

To identify the test line, the difference between the optical characteristics of a portion which is presumed to be the test line, and the optical characteristics of the ground of the test strip, can be compared with a threshold value, and the portion above-mentioned can be identified as the test line when the difference is greater than the threshold value. This prevents noise from being erroneously judged as the test line.

According to the present invention, a test strip measuring method comprises the steps of: detecting the optical characteristics C of a control line which has appeared on a test strip; detecting the optical characteristics R of the ground of the test strip; detecting the optical characteristics T of a test line which has appeared on the test strip; and conducting a quantitative measurement or a qualitative judgment on the test strip with use of a determinant and a reference value. The determinant is based on the difference or ratio between R and T, and the reference value is based on the difference or ratio between C and R.

This method is premised on the use of a test strip on which a control line will appear. According to this method, the variations in the measuring condition can be absorbed by measuring the control line, and the variations in optical characteristics of the grounds of test strips can be absorbed by detecting the optical characteristics R of the ground of the test strip. This achieves a more accurate quantitative measurement or qualitative judgment on a test strip.

The present invention may be arranged such that there is estimated the point of time when the control line will appear after the test strip has started moving, or the position where the control line will appear, and it is judged that the test strip is defective or the inspection is erroneous when the control line did not appear at the estimated point of time or in the estimated position. The present invention may be arranged such that after the control line has appeared, there is estimated the point of time when the test line will appear, or the position where the test line will appear, and a judgment of negativity is made when the test line did not appear at the estimated point of time or in the estimated position. In each of the arrangements above-mentioned, it is possible to prevent the control line or the test line from being erroneously detected.

The present invention may be arranged such that the test strip is held by a test strip holder, the test strip holder is detected at the time of the start of test strip movement, there is measured a period of time T1 from the start of test strip movement to the point of time when the forefront end of the test strip in the moving direction, has been detected, and there is estimated, based on the period of time T1, a period of time T2 after which the control line will appear. In such an arrangement, the period of time after which the control line will appear, can accurately be estimated or determined even though test strip holders are different in moving speed from one another.

The present invention may be arranged such that after the control line has appeared, there is estimated the point of time T3 when the test line will appear, and a judgment of negativity is made when the test line did not appear at the estimated point of time T3. In such an arrangement, the period of time after which the test line will appear, can accurately be estimated or determined even though test strip holders are different in moving speed from one another.

The present invention may be arranged such that to identify the test line, the difference between the optical characteristics of a portion which is presumed to be the test line, and the optical characteristics of the ground of the test strip, is compared with a threshold value, and the portion above-mentioned is identified as the test line when the difference is greater than the threshold value, and that to identify the control line, the difference between the optical characteristics of a portion which is presumed to be the control line, and the optical characteristics of the ground of the test strip, is compared with a threshold value, and the portion above-mentioned is identified as the control line when the difference is greater than the threshold value. In such an arrangement, it is possible to prevent noise from being erroneously judged as the test line or control line.

According to the present invention having the arrangement above-mentioned, the variations in the optical characteristics of the grounds of test strips can be absorbed, thus achieving an accurate quantitative measurement or qualitative judgment on each test strip.

Even though measuring devices are different in test strip moving speed from one another, the control line or test line can securely be identified.

According to the present invention, a test strip measuring device comprises: a test strip holding table arranged to be reciprocatingly movable; locking/unlocking means which is capable of locking the table to the main body of the test strip measuring device when the table is moved up to the innermost part, and which is capable of releasing this locked state; biasing means for resiliently biasing the table in the direction in which the table springs out from the innermost part; and resistance giving means for giving resistance to the motion of the table in the direction in which the table springs out from the innermost part.

According to the arrangement above-mentioned, when the table is unlocked and springs out with the test strip held, the table springs out at a limited speed under the action of the resistance giving means. Accordingly, even without the use of a motor for moving the table as conventionally done, the present invention can achieve, with a simple arrangement, a test-strip movement similar to that in the prior art.

The table is arranged to automatically travel at a uniform speed.

The present invention may be arranged such that the locking/unlocking means is arranged to lock the table when the table is pushed in, and to release this locked state when the table is again pushed in. Such an arrangement can start a coloration measurement on a test strip with a very simple operation.

The present invention may be arranged such that the table has a rack, and the resistance giving means is arranged to give a rotational resistance to a gear connected to the rack. Such an arrangement can readily give resistance to the table which presents a linear motion.

The present invention may be arranged such that the table has a rack, and the biasing means is arranged to rotationally bias a gear connected to the rack. Such an arrangement can readily bias the table which presents a linear motion.

BRIEF DESCRIPTION OF THE DRAWINGS

FIG. 6A to FIG. 6D are views illustrating the relationship between the locking member 3b and a pin 13, in which FIG. 6A illustrates the state where the test strip holding table 3 is being inserted, FIG. 6B illustrates the engagement position, and each of FIGS. 6C and 6D illustrates the state where the locked state has been released;

FIG. 11A is a graph of typical reflective intensity data, while FIG. 11B is a graph obtained by differentiating the data in FIG. 11A;

DESCRIPTION OF THE PREFERRED EMBODIMENTS

Figure 1:
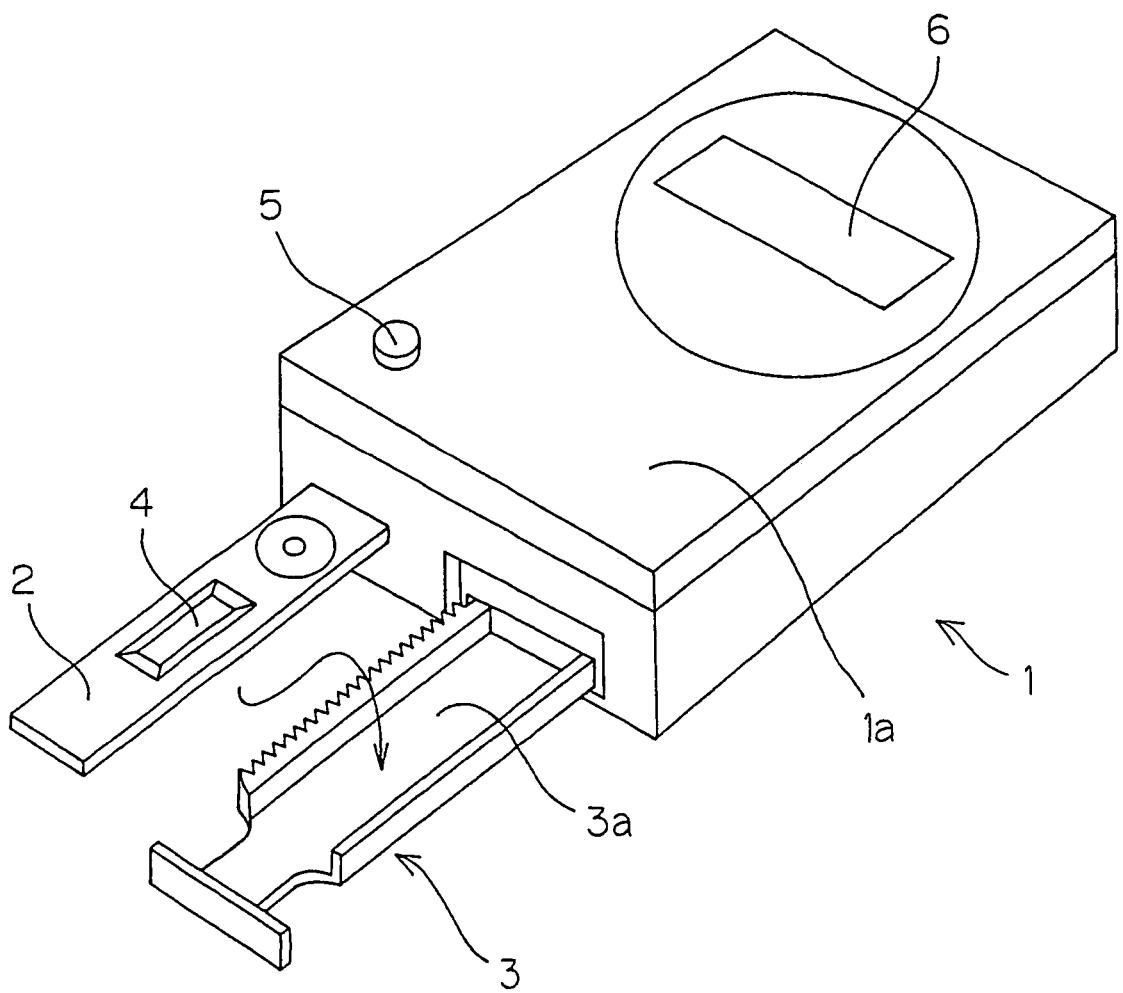
FIG. 1 is a schematic perspective view of a test strip measuring device of the present invention.

FIG. 1 is a schematic perspective view of a test strip measuring device of the present invention. The test strip measuring device comprises a test strip measuring device main body 1 and a test strip holder 2 to be changed for each measurement.

The test strip measuring device main body 1 comprises a test strip holding table 3 arranged to be reciprocatingly movable, a display 6 for displaying a measurement result such as positivity, negativity or the like, and a power switch 5. The test strip holding table 3 has a concave portion 3a in which a test strip holder 2 is to be set.

The test strip holder 2 holds a test strip 4 in a unitary structure and is to be thrown away after the measurement is completed.

Figure 2:
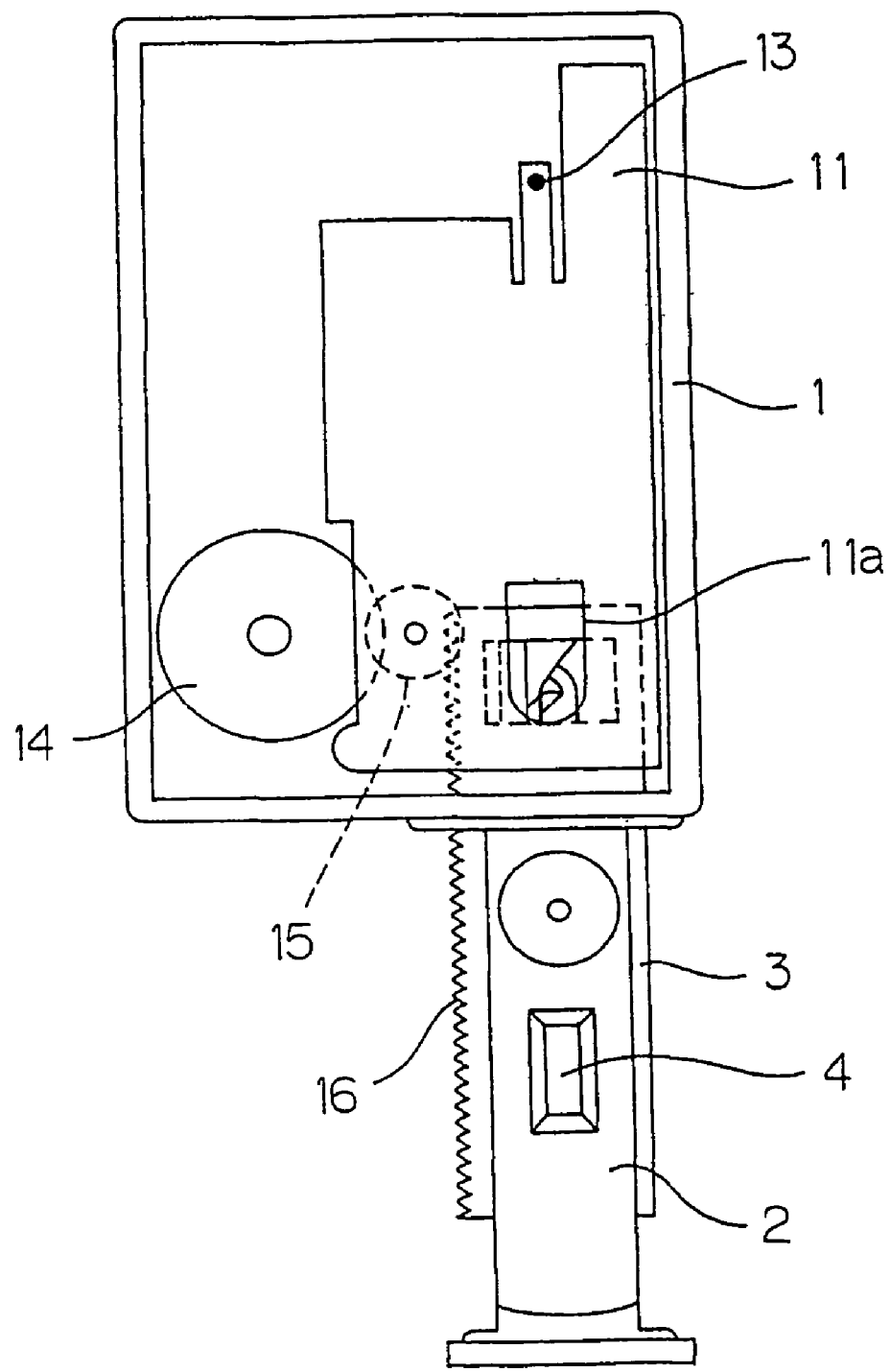
FIG. 2 is a plan view of the test strip measuring device with an upper cover 1a and a circuit board secured thereto removed.

FIG. 2 is a plan view of the test strip measuring device with an upper cover 1a and a circuit board secured thereto removed.

The test strip measuring device main body 1 has a partition plate 11 for defining a space into which the test strip holding table 3 is introduced. The partition plate 11 has a pin 13 which project downwardly (to the reverse side of the paper plane of FIG. 2) from the partition plate 11.

The partition plate 11 has a window 11a through which a test strip 4 is to be optically measured. The test strip holding table 3 is to be inserted under the partition plate 11.

Figure 3:
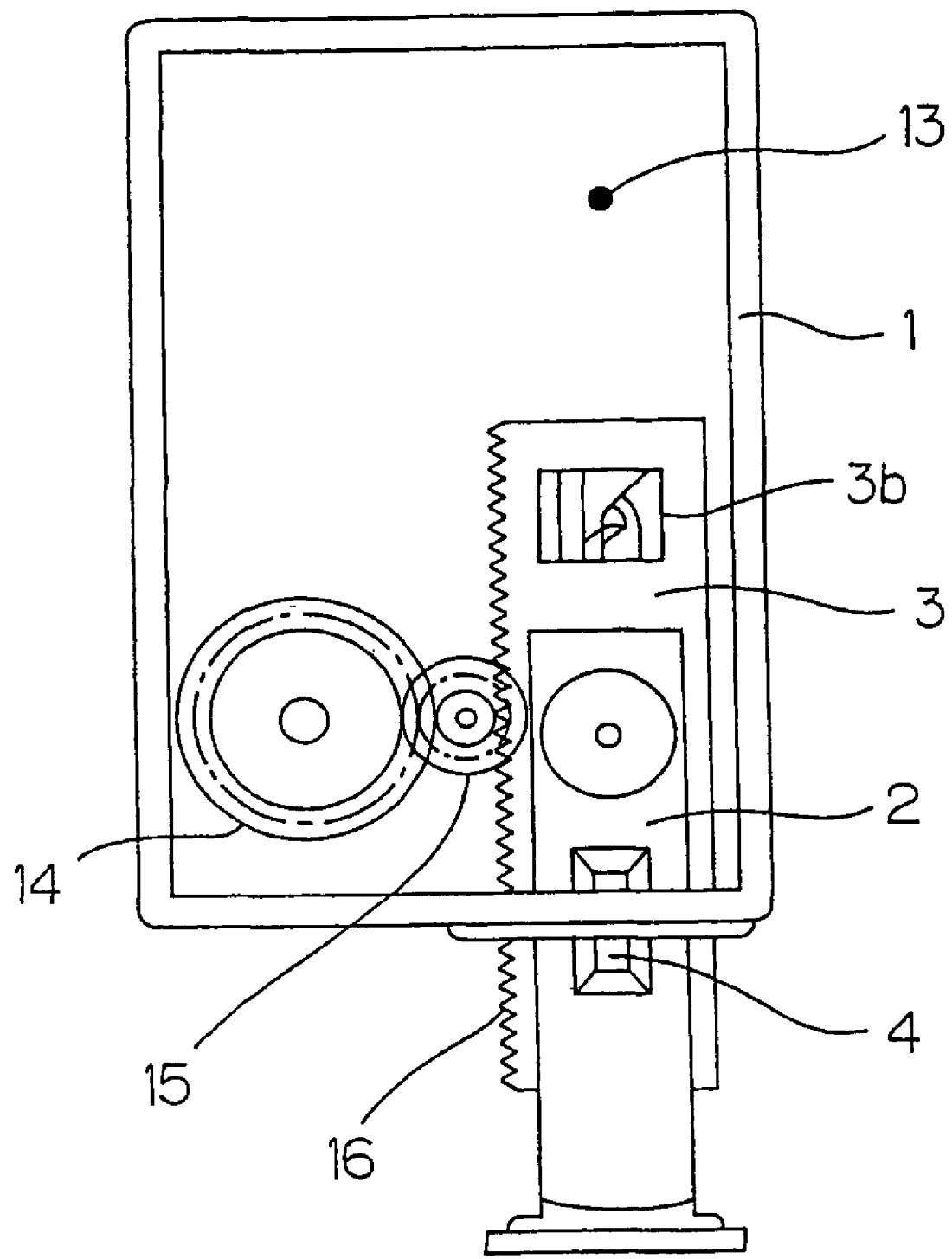
FIG. 3 is a plan view of the test strip measuring device with a partition plate 11 removed.
Figure 7:
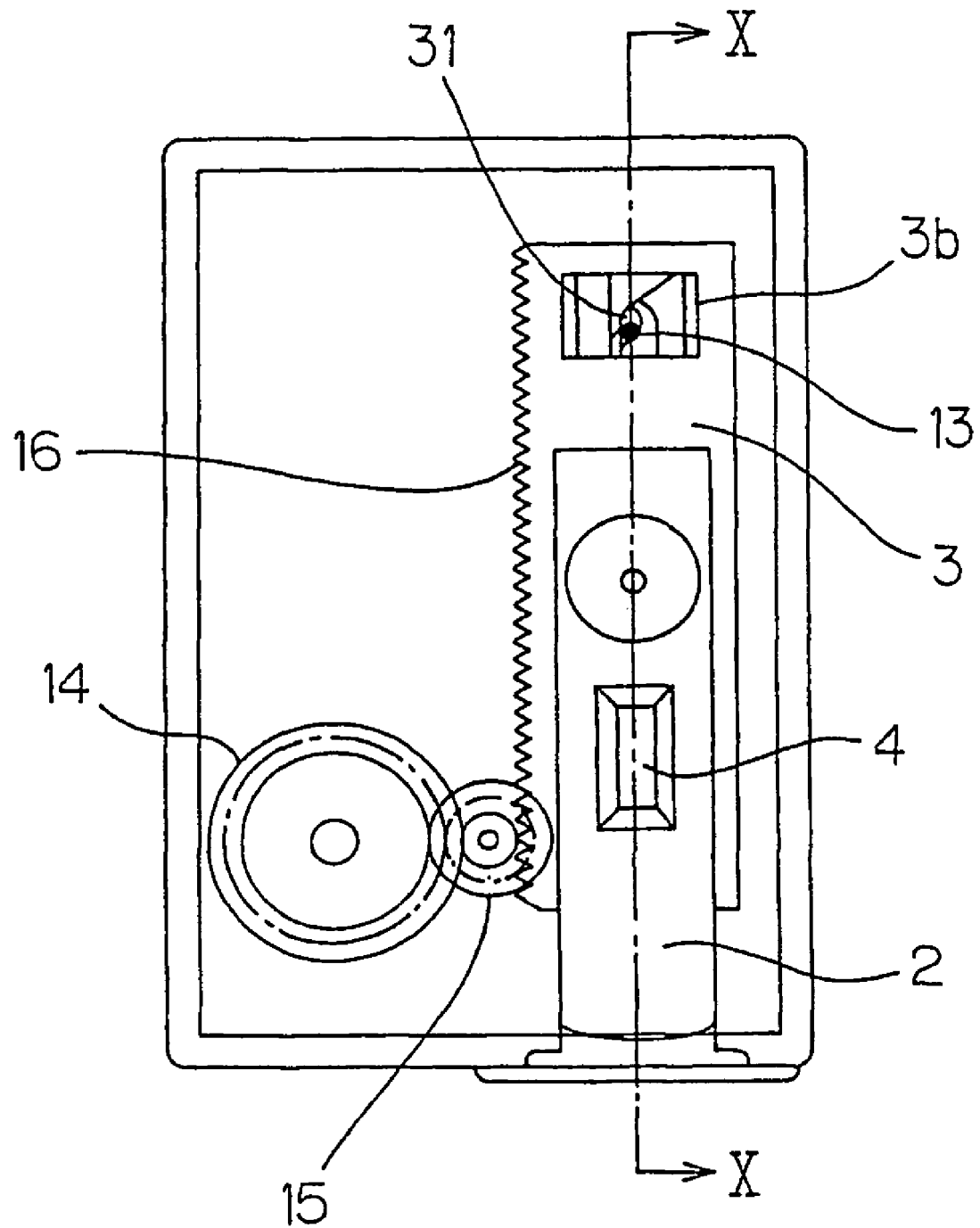
FIG. 7 is a plan view illustrating the state where the test strip holding table 3 is being pushed in to the innermost part such that the table 3 is locked.

FIG. 3 is a plan view with the partition plate 11 removed (The pin 13 secured to the partition plate 11 is actually not seen, but is imaginarily illustrated in FIGS. 3 and 7). The rectangular test strip holding table 3 is so disposed as to be inserted into the test strip measuring device main body 1, and is provided at one side thereof with a rack 16. The test strip measuring device main body 1 has an idle gear 15 to be meshed with the rack 16, and a drive gear 14 to be meshed with the idle gear 15.

A viscous damper (not shown) is mounted on the idle gear 15. For example, the viscous damper is made in the form of an impeller which is rotatable in association with the idle gear 15 and which is disposed in a viscous body such as grease.

The drive gear 14 is resiliently biased to one rotational direction by a torsion coiled spring. The biasing direction corresponds to the direction in which the test strip holding table 3 springs out from the test strip measuring device main body 1.

Figure 4:
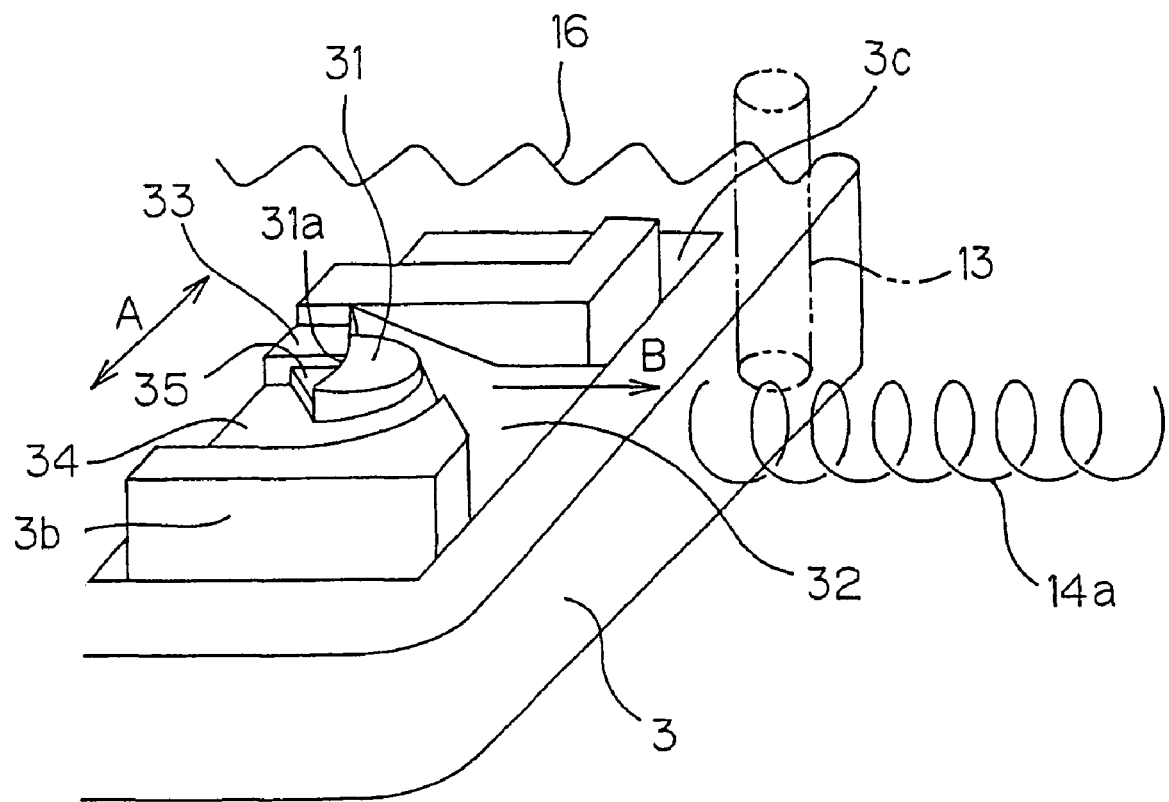
FIG. 4 is a perspective view of an example in which a compression coiled spring 14a is used as biasing means for biasing a test strip holding table 3.

The biasing means for biasing the test strip holding table 3 is not limited to the drive gear 14 incorporating a torsion coiled spring. There may be adopted other known means such as a compression coiled spring 14a for pushing one end of the test strip holding table 3 as shown in FIG. 4.

The test strip holding table 3 has a locking member 3b which locks the test strip holding table 3 with respect to the test strip measuring device main body 1 when the test strip holding table 3 is pushed in to the innermost part, and which releases this locked state by a predetermined operation. Together with the pin 13 mentioned earlier, this locking member 3b forms locking/unlocking means.

Figure 5:
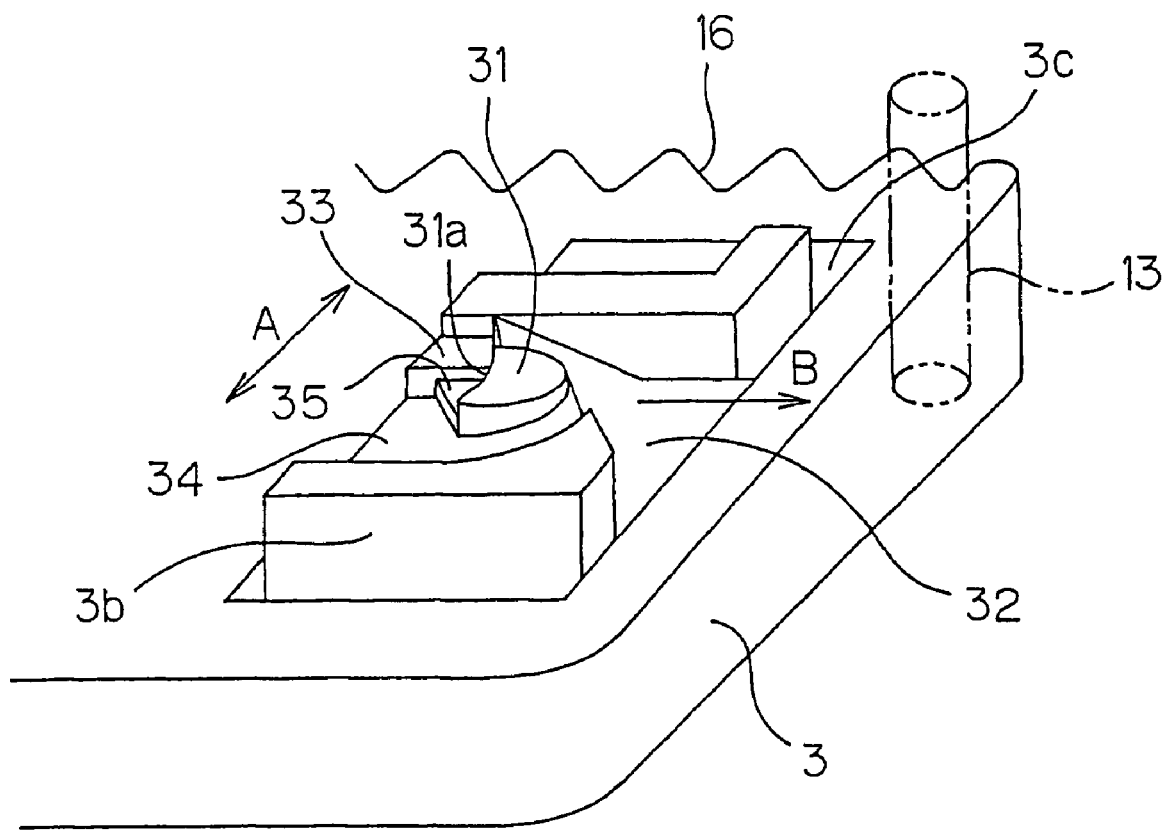
FIG. 5 is a perspective view illustrating a locking member 3b mounted on the test strip holding table 3.

FIG. 5 is a perspective view illustrating the locking member 3b mounted on the test strip holding table 3. The locking member 3b is made of a readily sliding resin (ex. nylon), and is so mounted in a concave portion 3c formed in the test strip holding table 3 as to be movable in directions A at right angles to the insertion direction B of the test strip holding table 3. The locking member 3b includes, as shown in FIG. 5, grooves 32, 33 and 34 for introducing the pin 13, a step portion 35 and a projection 31 for engaging with the pin 13.

When the test strip holding table 3 is inserted, a groove 32 of the locking member 3b is moved up to the position of the pin 13. The groove 32 is gradually raised and then vertically falls down to communicate with a groove 33. The groove 33 falls down in the transverse direction to communicate with a lower groove 34. The groove 34 is raised arcuately as if surrounding a projection 31 and then vertically falls down to communicate with the groove 32.

The projection 31 is disposed at that center of the locking member 3b which is surrounded by the grooves 32, 34. The projection 31 has a concave portion 31a with which the pin 13 is to be engaged. Disposed under the concave portion 31a is a step portion 35 for introducing the pin 13.

FIG. 6A to FIG. 6D illustrate the engagement operations of the locking member 3b with respect to the pin 13. FIG. 6A illustrates the state where the test strip holding table 3 is being inserted, FIG. 6B illustrates the engagement position and each of FIGS. 6C and 6D illustrates the state where the locked state has been released. The gap between the locking member 3b and the concave portion 3c is generally designated by 99.

When the test strip holding table 3 is inserted, the pin 13 is introduced into the groove 32 (FIG. 6A). When the test strip holding table 3 is further inserted, the pin 13 falls in the groove 33. The boundary between the grooves 32, 33 is inclined in plan elevation. Accordingly, when the operator's hand is left from the test strip holding table 3, the locking member 3b receives force in the upward direction with respect to the paper plane, causing the locking member 3b to be moved upward. Accordingly, the pin 13 is fitted, through the step portion 35, to the concave portion 31a of the locking member 3b (FIG. 6B). This locks the test strip holding table 3.

Then, when the test strip holding table 3 is pushed a little bit, the pin 13 falls down from the step portion 35 to the groove 34. When the operator's hand is left from the test strip holding table 3, the test strip holding table 3 starts moving because the table 3 is receiving force in the left direction on the drawing paper, from the drive gear 14. At this time, the locking member 3b receives force in the upward direction with respect to the paper plane and is moved upward because the boundary between the step portion 35 and the groove 34 is obliquely defined. Accordingly, the pin 13 is not returned to the concave portion 31a, but falls in the groove 34 (FIG. 6C).

When the test strip holding table 3 is further moved, the pin 13 is raised along the groove 34, then falls in the groove 32 and is then left from the locking member 3b.

As discussed in the foregoing, the test strip holding table 3 can be locked with respect to the test strip measuring device main body 1 when the test strip holding table 3 is pushed to the innermost part, and this locked state can be released when the test strip holding table 3 is pushed again.

FIG. 7 is a plan view illustrating the locked state where the test strip holding table 3 is pushed in to the innermost part. By the engagement of the pin 13 with the projection 31 of the locking member 3b, the test strip holding table 3 is locked.

Figure 8:
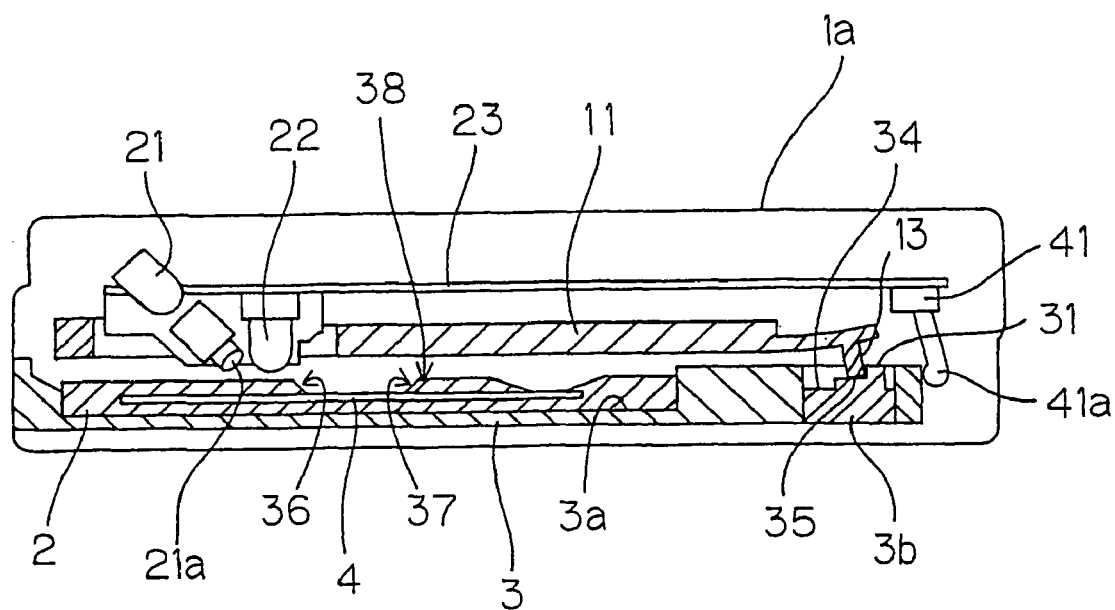
FIG. 8 is a section view, taken along the line X-X in FIG. 7, illustrating the locked state.

FIG. 8 is a section view taken along the line X-X of FIG. 7 illustrating the locked state. The upper cover 1a and the circuit board 23 secured thereto are also illustrated. The pin 13 is placed on the step portion 35 of the locking member 3b and engaged with the concave portion 31a.

As the locking/unlocking releasing means, there may be used known means other than that shown in FIGS. 6 and 7.

Disposed on the circuit board 23 are a light projecting portion 21 having an LED, a light receiving portion 22 having a photodiode, and a switch 41 for detecting the position of the test strip holding table 3. A lens 21a is disposed at the tip of the light projecting portion 21 for adjusting the focus to the surface of the test strip 4. The light emitting wavelength of the LED is set to that of light to be absorbed by a mark which will appear on the test strip 4 (For example, the LED emits green light when the mark appearing on the test strip 4 is red). The switch 41 has a rotatable arm 41a. By sensing the position of the arm 41a, the insertion/removal of the test strip holding table 3 is detected.

In the arrangement above-mentioned, when the test strip holding table 3 is released from the locked state, the test strip holding table 3 springs out substantially at a uniform rate (hereinafter referred to as "automatic traveling"), and the switch 41 is actuated. During the automatic traveling, the reflective intensity of the test strip 4 is measured with the passage of time.

The following description will discuss a test strip measuring method in which a test strip 4 held in the test strip holding table 3 is continuously measured during the automatic traveling of the test strip holding table 3.

<First Test Strip Measuring Method>

Figure 9:
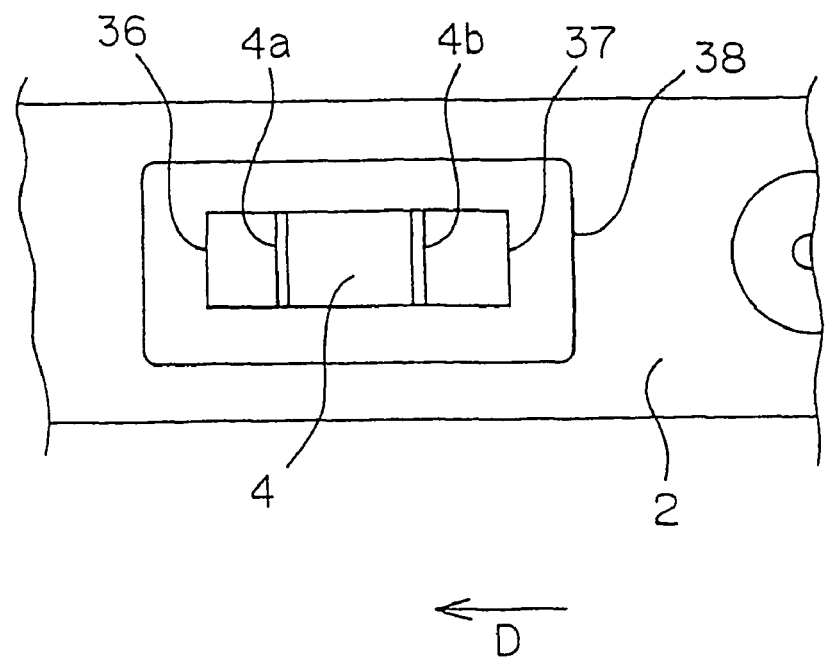
FIG. 9 is a view illustrating the positions of marks appeared on a test strip 4.

FIG. 9 is a view illustrating the positions of marks which have appeared on the test strip 4. An arrow D in FIG. 9 shows the automatic traveling direction of the test strip holding table 3. Generally, two colored lines of a control line 4a and a test line 4b will appear on the test strip 4. In the present invention, the control line 4a is used for obtaining a reference value based on which the reflective intensity of the test line 4b is judged.

In the following description, the reflective intensity of the test line 4b, the reflective intensity of the control line 4a and the reflective intensity of the ground of the test strip 4 are respectively designated by T, C, R.

Figure 10:
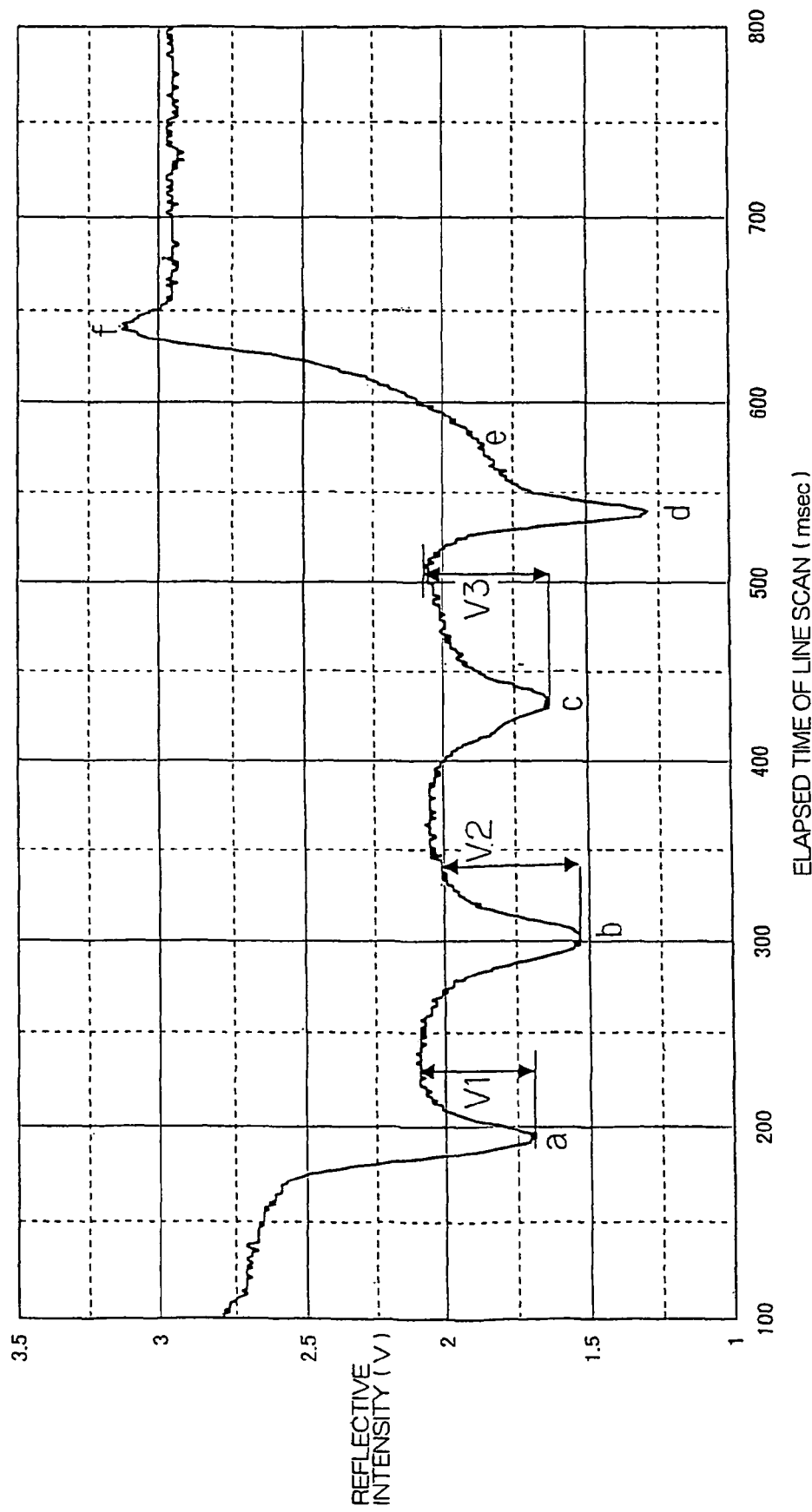
FIG. 10 is a graph illustrating the continuous measurement results (in the case of a positive reaction) of a test strip during the automatic traveling of the test strip holding table 3.

FIG. 10 is a graph illustrating the continuous measurement results of the test strip 4 during the automatic traveling of the test strip holding table 3 which holds the test strip holder 2. The axis of ordinates represents reflective intensity (represented in voltage in FIG. 10, but the unit is optional), while the axis of abscissa represents the elapsed time of automatic traveling (in msec) after the switch 41 has changed from ON to OFF. The larger a value in the axis of ordinates is, the stronger the reflective intensity is.

In this graph, there appear four valleys a, b, c, d, an intermediate portion e, and a mountain f. The first appearing valley a represents an edge 36 of the test strip exposing window of the test strip holder 2. The next appearing valley b represents the control line 4a, the next valley c represents the test line 4b, and the next valley d represents an edge 37 of the test strip exposing window of the test strip holder 2. The mountain f represents an edge 38 of the test strip exposing window of the test strip holder 2. The portions between the valleys a and b, between the valleys b and c, and between the valleys c and d, represent the ground portions of the test strip 4.

The following description will discuss a test strip measuring method executed by a microcomputer mounted on the circuit board 23.

Figure 11:
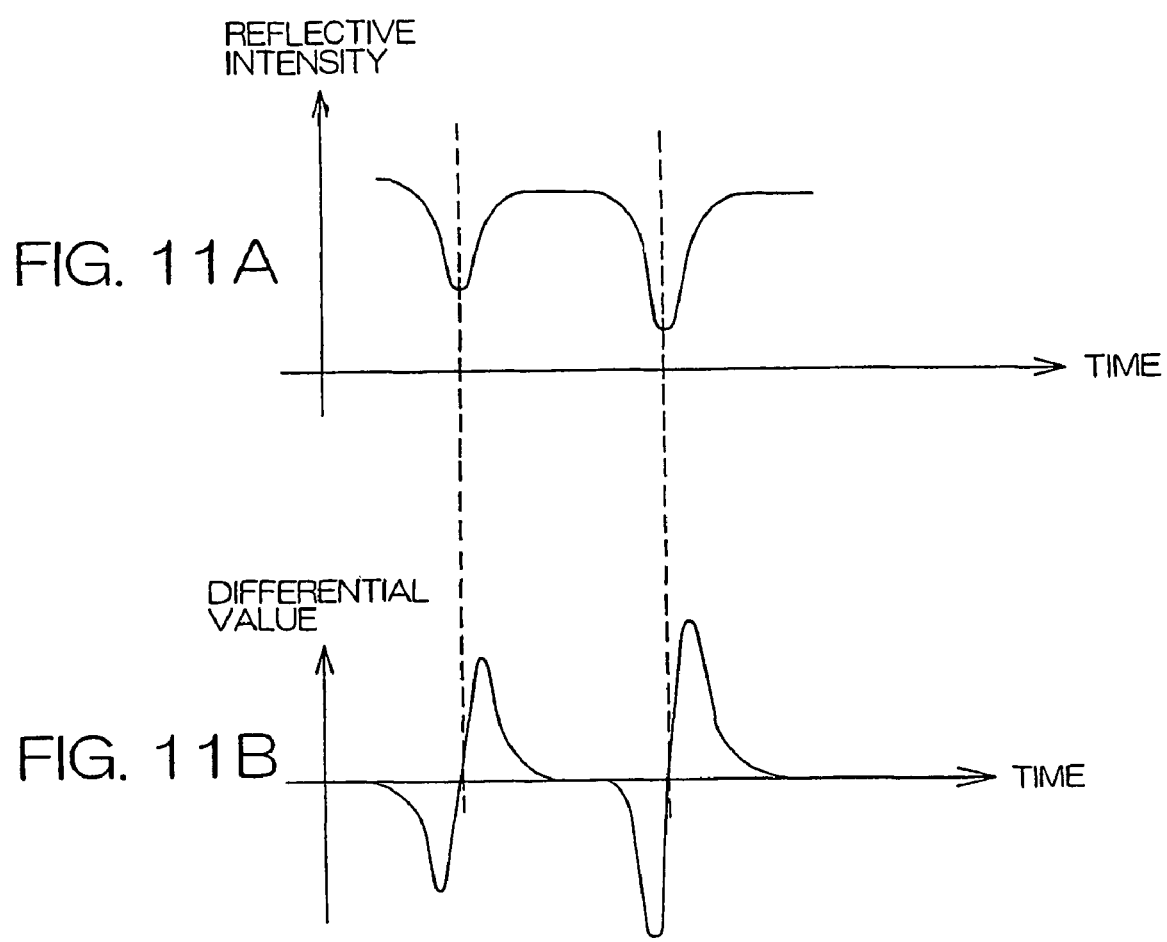

Based on the data obtained by differentiating the graph of reflective intensity in FIG. 10, the positions of valleys or mountains are judged. For example, when a graph of reflective intensity includes valleys as shown in FIG. 1A, the curve obtained by differentiating the graph in FIG. 11A is as shown in FIG. 1B. Accordingly, a zero-cross point from a negative value to a positive value, is defined as a valley portion, while a zero-cross point from a positive value to a negative value is defined as a mountain.

During the automatic traveling, the difference between the appearing valley a and the subsequent mountain portion (See V1 in FIG. 10), is obtained. When this difference exceeds, for the first time, a first threshold value (for example, 32 mV), the valley a is regarded as the edge 36 of the test strip exposing window. The difference is compared with the first threshold value in order to eliminate small irregularities appearing due to noise.

The difference between the subsequently appearing valley b and the subsequent mountain portion (See V2 in FIG. 10) is obtained. When this difference exceeds a second threshold value (for example 64 mV), the valley b is regarded as the control line 4a. This difference is compared with the second threshold value in order to eliminate small irregularities appearing due to noise.

The difference between the subsequently appearing valley c and the subsequent mountain portion (See V3 in FIG. 10) is obtained. When this difference is larger than a third threshold value (for example 26 mV) and less than a fourth threshold value (for example 100 mV), the valley c is regarded as the test line 4b. The difference is compared with the third threshold value in order to eliminate small irregularities appearing due to noise. The fourth threshold value is used for detecting the edges 37, 38.

Figure 12:
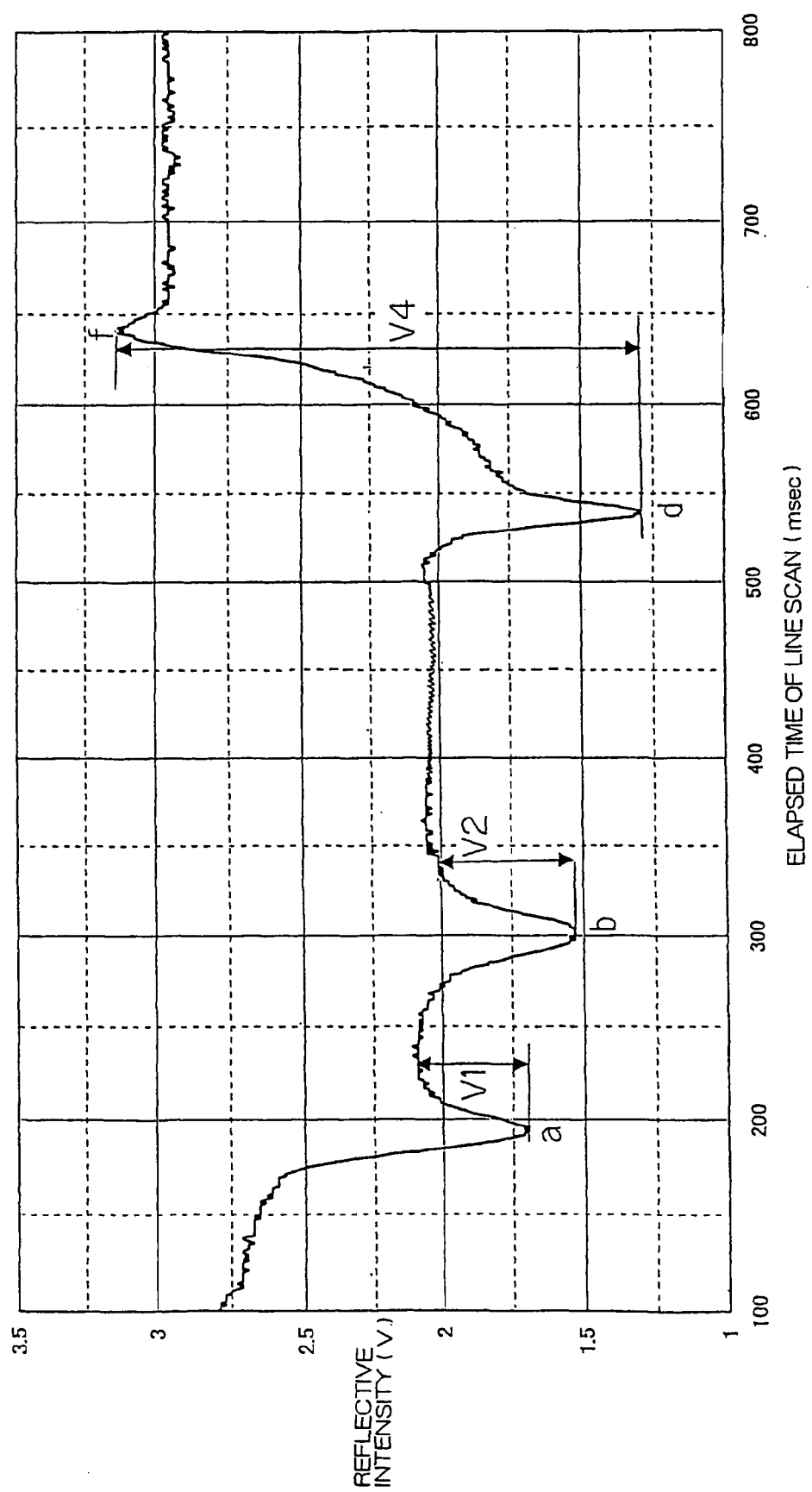
FIG. 12 is a graph illustrating the continuous measurement results (in the case of a negative reaction) of a test strip during the automatic traveling of the test strip holding table 3.

The foregoing shows the judgment of a positive reaction. In the case of a negative reaction, the valley c does not appear as shown in FIG. 12. The microcomputer recognizes the subsequently appearing valley d as the valley c. When the difference between the valley d and the mountain f (See V4 in FIG. 12) exceeds the fourth threshold value, it is regarded that the valley c did not exist, i.e., the test line 4b was not detected. Thus, there is made a judgment that the specimen is negative.

The judgments above-mentioned mean that there have been identified the valley b based on the control line 4a, the valley c based on the test line 4b, and the mountain portions.

Here, the reflective intensity of the control line 4a at the valley b, the reflective intensity of the test line 4b at the valley c, and the reflective intensity of the ground of the test strip 4, are respectively designated by C, T, R. The reflective intensity R of the ground may be defined as (1) the peak value of the mountain portion between the valleys b and c, or (2) the center value or average value of the peak values of the respective mountain portions.

The microcomputer obtains a determinant DET according to the following equation:

$$DET=(R-T)/(R-C)$$

According to this equation, the influence of the ground is eliminated by obtaining the difference between the reflective intensity T of the test line 4b and the reflective intensity R of the ground, and by obtaining the difference between the reflective intensity C of the control line 4a and the reflective intensity R of the ground. Further, the influence of the test conditions (for example, difference among samples, difference among test strips, etc.) is eliminated by dividing (R–T) of the reflective intensity of the test line 4b with the influence of the ground eliminated, by (R–C) of the reflective intensity of the control line 4a with the influence of the ground eliminated, this (R–C) serving as a reference value.

To obtain the determinant DET, the following equation may also be used:

$$DET=(R/T)-(R/C)$$

According to this equation, the influence of the ground is eliminated by obtaining the ratio between the reflective intensity T of the test line 4b and the reflective intensity R of the ground, and by obtaining the ratio between the reflective intensity C of the control line 4a and the reflective intensity R of the ground. Further, the influence of the test conditions is eliminated by subtracting (R/C) of the reflective intensity of the control line 4a with the influence of the ground eliminated, from (R/T) of the reflective intensity of the test line 4b with the influence of the ground eliminated, this (R/C) serving as a reference value.

The microcomputer stores threshold values T1, T2 for qualitative judgment (0<T1<T2<1). By comparing the obtained determinant DET with the threshold values T1, T2, it is judged that the specimen is negative, quasi-positive, or positive. More specifically, the specimen is judged as negative when 0<DET<T1, the specimen is judged as quasi-positive when T1<DET<T2, and the specimen is judged as positive when T2<DET<1. The threshold values T1, T2 may be determined by conducting tests on a number of specimens and selecting a value with which the qualification of patients can be reproduced most accurately.

The microcomputer displays, on the display 6, the numerical value of the determinant DET obtained in the manner above-mentioned, and the judgment result such as negativity, quasi-positivity, positivity.

<Second Test Strip Measuring Method>

The following description will discuss a second test strip measuring method improved in identification of a control line or a test line appearing on a test strip 4.

According to the first test strip measuring method, a valley position is identified by comparing the difference in reflective intensity between valley and mountain, with a threshold value.

According to the second test strip measuring method, consideration is taken not only on the reflective intensities of valley and mountain, but also on the point of time when a valley appears. This further lowers the rate of erroneous detection of a valley position, enabling an accurate valley position to be identified.

According to the second test strip measuring method, the edges 36, 37, 38 of the test strip holder 2 are made smooth in shape such that these edges 36, 37, 38 do not appear in the measured intensity data. Accordingly, if there is no noise, the first appearing valley during the test corresponds to the control line 4a, and the next appearing valley corresponds to the test line 4b.

Figure 13:
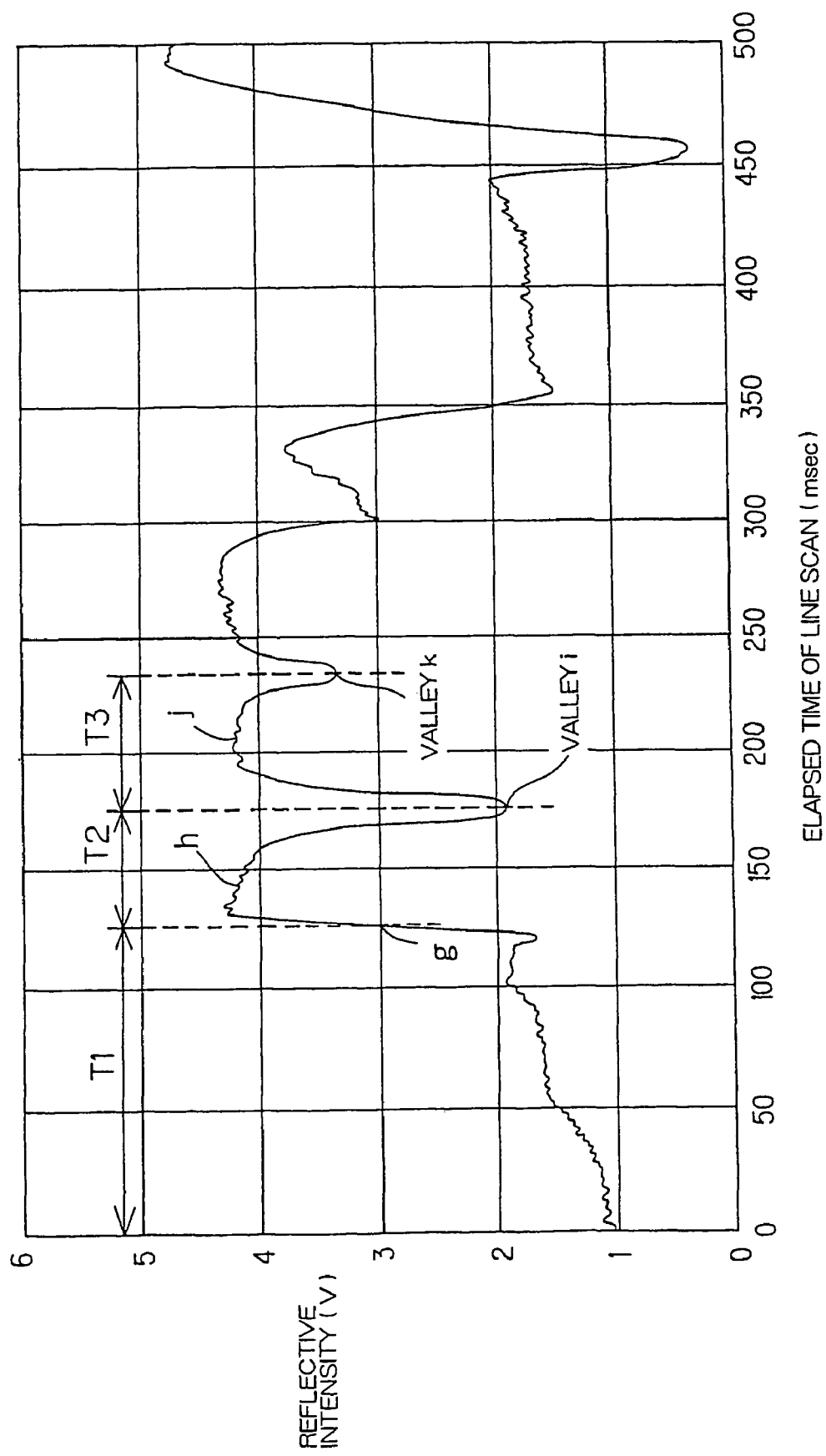
FIG. 13 is a graph illustrating the continuous measurement results of a test strip during the automatic traveling of the test strip holding table 3 which holds a test strip holder 2.
Figure 14:
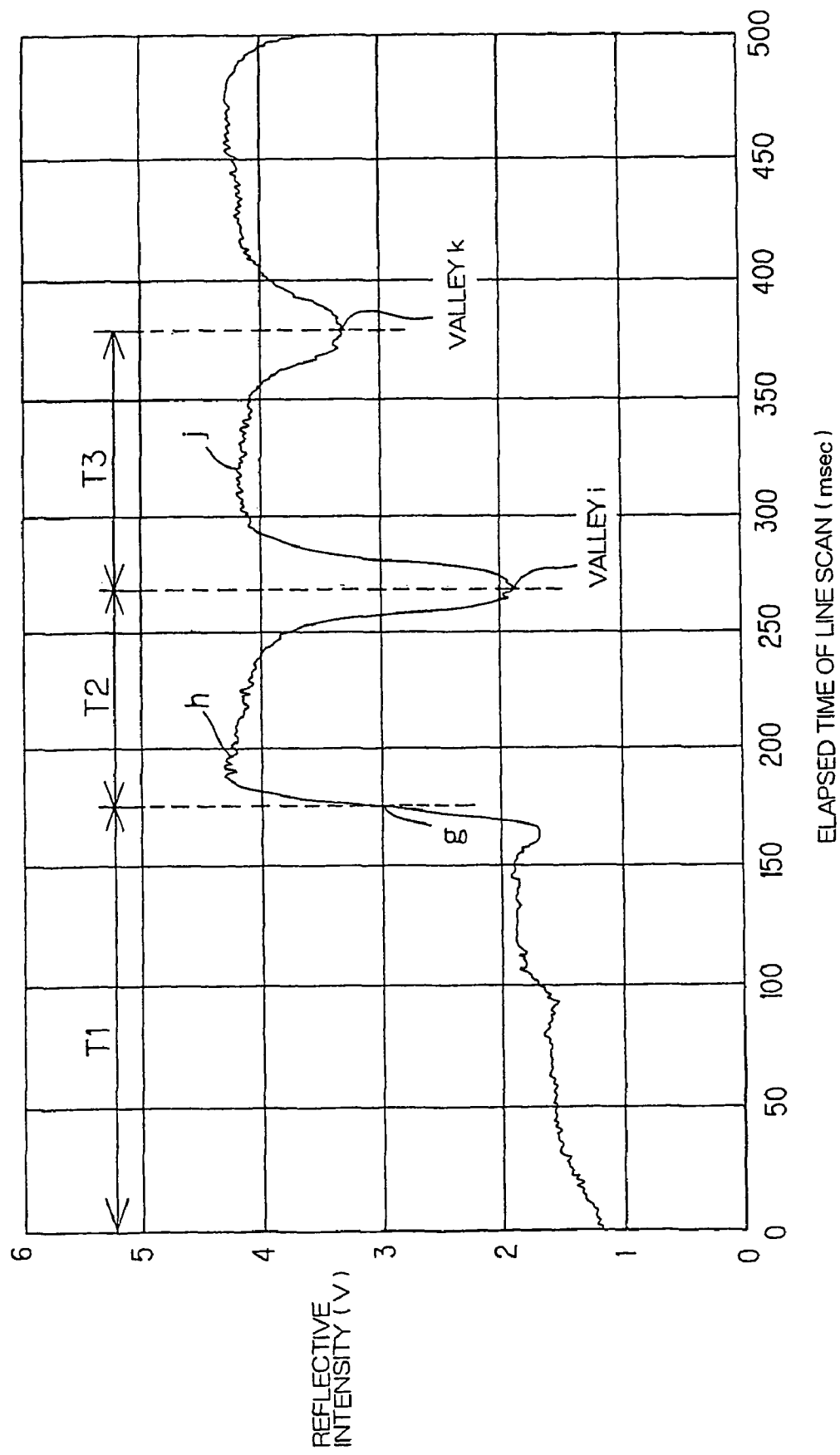
FIG. 14 is a graph illustrating the continuous measurement results of a test strip during the automatic traveling of the test strip holding table 3 which holds the test strip holder 2.

Each of FIGS. 13 and 14 is a graph illustrating the continuous measurement results of a test strip during the automatic traveling of the test strip holding table 3 which holds a test strip holder 2. The axis of ordinates represents reflective intensity (in voltage in FIGS. 13 and 14, but the unit is optional), while the axis of abscissa represents the elapsed time of line scan (in msec). FIG. 13 and FIG. 14 are different from each other in the automatic traveling speed of the test strip holding table 3 due to the difference in the viscous resistance of the damper or the difference in the hardness of the coiled spring. Even though there is difference in automatic traveling speed, the following processing is the same.

In each graph, two valleys i, k appear. The first appearing valley i represents the control line 4a, and the next appearing valley k represents the test line 4b. A mountain h before the valley i, and a mountain j between the valleys i, k, represent the ground portions of the test strip 4.

Figure 15:
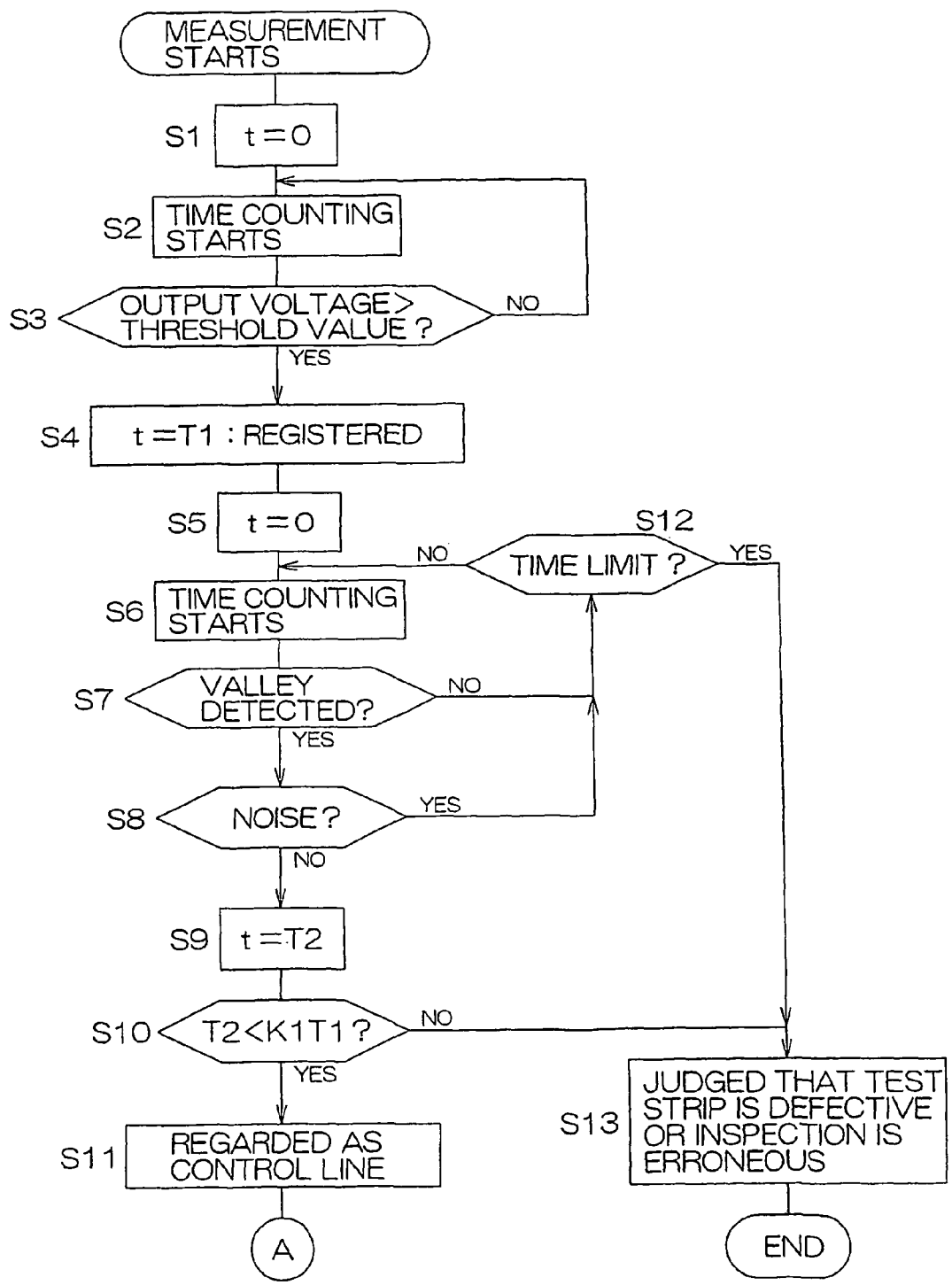
FIG. 15 is a flow chart illustrating a test strip measuring method executed by a microcomputer.

FIG. 15 is a flow chart illustrating the second test strip measuring method executed by a microcomputer.

At the time when the switch 41 is changed from ON to OFF (measurement starting point of time), time counting starts (Steps S1, S2). When the forefront end of the test strip in the moving direction, is detected during the automatic traveling of the test strip holding table 3, the output voltage of the light receiving portion 22 is increased. At the time when the output voltage exceeds a threshold value (3V)(Step S3), a time count value T1 is registered (Step S4). This time count value T1 represents a distance L1 between the detection position of the light receiving portion 22 at the time when the switch 41 is changed from ON to OFF immediately after the start of automatic traveling of the test strip holding table 3, and the forefront end of the test strip in the moving direction.

Thereafter, time counting starts (Steps S5, S6), and it is judged whether or not a valley has been detected (Step S7) and whether or not the detected valley corresponds to noise (Step S8). This valley judgment may be made by a differentiation method as discussed in connection with FIG. 11A and FIG. 11B. The judgment of noise may be made, as discussed earlier, by comparing the difference between the valley and the subsequently appearing mountain portion, with the threshold value.

When there is detected the valley i which is not corresponding to noise, the time count value t at the time of this valley detection, is set to T2 (Step S9) and it is judged whether or not T2 is smaller than $k1 \cdot T1$ (Step S10).

$$T2 < k1 \cdot T1$$

The coefficient $k1$ is set to a value which is equal to or slightly larger than the ratio between a distance L2 from the forefront end of the test strip in the moving direction, to the control line, and the distance L1 above-mentioned. Accordingly, $k1$ is a constant having no relation to the automatic traveling speed of the test strip holding table 3.

When $T2 < k1 \cdot T1$, the microcomputer regards this valley i as the control line (Step S11). When $T2 \geq k1 \cdot T1$, this means that the control line could not be detected at the position where the control line must appear. It is therefore judged that the test strip is defective or the inspection is erroneous (Step S13).

Further, when no valley is detected within the time limit (Step S12) or when all the valleys detected correspond to noise, it is judged that the test strip is defective or the inspection is erroneous (Step S13). This time limit may be the same as the time $k1 \cdot T1$ above-mentioned.

Figure 16:
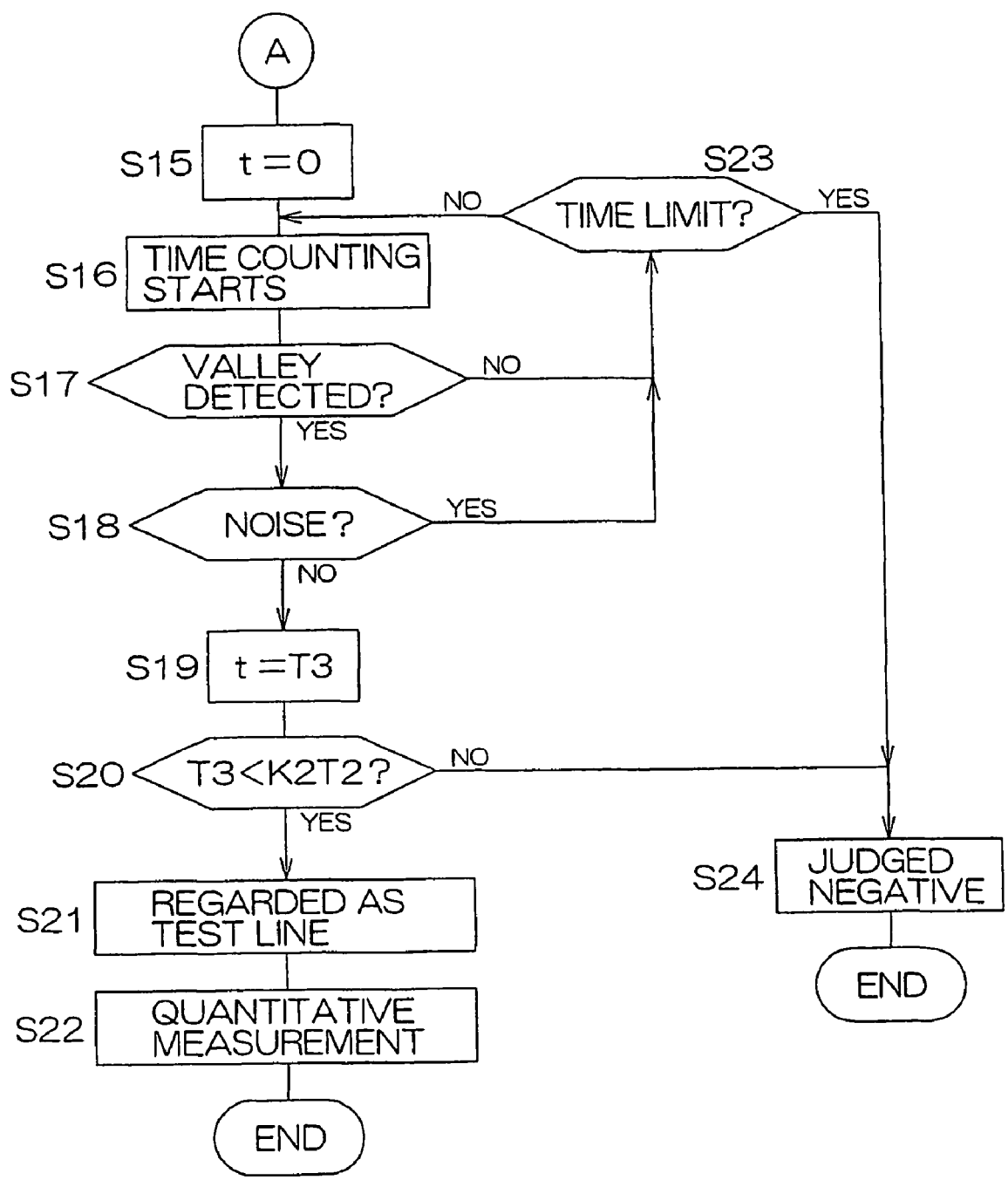
FIG. 16 is a flow chart (continuation) illustrating a test strip measuring method executed by the microcomputer.

FIG. 16 is a flow chart (continuation) illustrating the test strip measuring method executed by the microcomputer.

Time counting starts (Steps S15, 16), and it is judged whether or not a valley has been detected (Step S17), and it is judged whether or not the detected valley corresponds to noise (Step S18).

When there is detected a valley which does not correspond to noise, the time count value t at the time of this valley detection, is set to T3 (Step S19) and it is judged whether or not T3 is smaller than $k2 \cdot T2$ (Step S20).

$$T3 < k2 \cdot T2$$

The coefficient $k2$ is set to a value which is equal to or slightly larger than the ratio between a distance L3 from the control line of the test strip 4 to the test line thereof, and the distance L2 above-mentioned. Accordingly, $k2$ is also a constant having no relation to the automatic traveling speed of the test strip holding table 3.

The following formula may be used in place of the above one.

$$T3 < k3(T1+T2)$$

The coefficient $k3$ is set to a value which is equal to or slightly larger than the ratio between a distance L3 from the control line of the test strip 4 to the test line thereof, and the distance (L1+L2) above-mentioned. Accordingly, $k3$ is also a constant having no relation to the automatic traveling speed of the test strip holding table 3.

When the formula of Step S20 is satisfied, the detected valley is regarded as the test line (Step S21) and a quantitative measurement is conducted (Step S22). More specifically, there are calculated the reflective intensity C of the control line, the reflective intensity T of the test line, and the reflective intensity R of the ground of the test strip 4, and the following determinant DET is obtained:

$$DET=(R-T)/(R-C)$$

The microcomputer supplies this determinant DET.

Further, as mentioned earlier, the threshold values T1, T2 for qualitative judgment are stored. Then, it is judged that the specimen is negative, quasi-positive, or positive by comparing the obtained determinant DET with the threshold values T1, T2.

The microcomputer displays, on the display 6, the numerical value of the determinant DET obtained in the manner above-mentioned, and the judgment result such as negativity, quasi-positivity, positivity.

When the formula of Step S20 is not satisfied, this means that the test line could not be detected at the position where the test line must appear. It is therefore judged that the specimen is negative (Step S24).

Further, when no valley is detected within the time limit (Step S23) or when all the valleys detected correspond to noise, it is judged that the specimen is negative (Step S24). This time limit may be the same as the time $k2 \cdot T2$ or $k3 (T1+T2)$.

In the processing in FIGS. 15 and 16, the microcomputer executes time-counting to acquire the moving position of the test strip. Instead of such time-counting, a sensor may be disposed and linear graduations may be put on the test strip holding table 3 or the test strip holder 2, such that the sensor reads such graduations.

Figure 17:
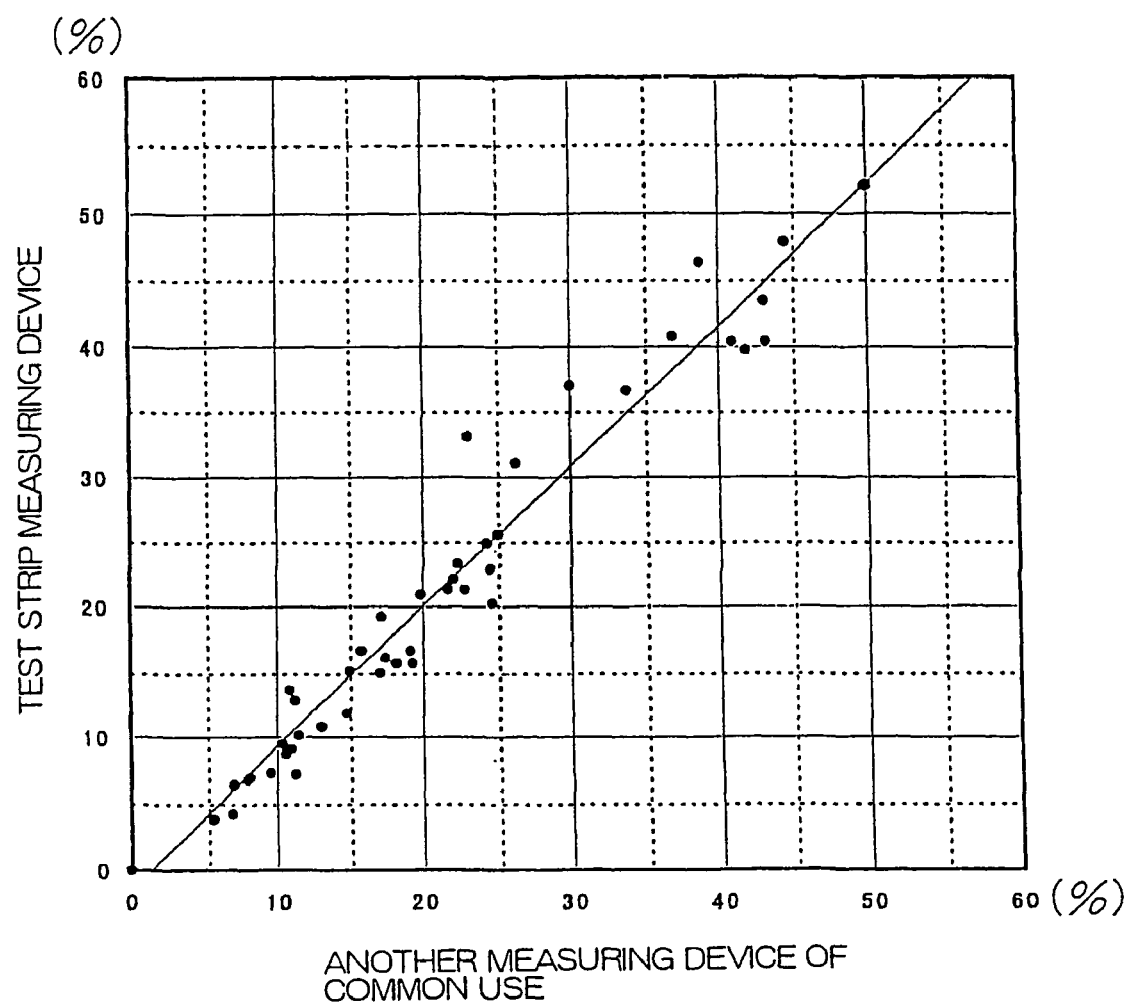
FIG. 17 is a graph illustrating the results obtained through measurements respectively conducted with the use of the test strip measuring device of the present invention and another measuring device of common use.

A numerical value obtained by quantitative measurement can be converted in terms of unit of common use in this industrial field. In this connection, a calibration curve is formed by respectively conducting measurements on same test strips with the use of the test strip measuring device of the present invention and with the use of other measuring device of common use. FIG. 17 is a graph illustrating an example of measurement results. The axis of abscissa represents the measured values obtained by conducting measurement with a known measuring device (Densitograph AE-6920 manufactured by ATTO Co., Ltd.) arranged to conduct measurement of test strip based on image data obtained by a CCD camera, while the axis of ordinates represents the measured values obtained by conducting measurement with the test strip measuring device of the present invention. When the measured values obtained by the test strip measuring device of the present invention are compared with the measured values obtained by other measuring device, there is established a correlation coefficient as high as about 0.981.

The linear line shown in the graph in FIG. 17, is a calibration curve prepared with the use of a method of least squares or the like. When this calibration curve is once obtained, the measured values obtained with the test strip measuring device of the present invention, can automatically be displayed as converted in terms of other unit.

The foregoing has discussed embodiments of the present invention. However, the present invention should not be limited to these embodiments, but a variety of modifications can be made within the scope of the invention. For example, there can be conducted a quantitative measurement or qualitative judgment even on a test strip having a plurality of control lines and/or a plurality of test lines, by applying the algorism in FIGS. 15 and 16 to each of the lines.

Further, for a test strip arranged such that no control line appears thereon, the influence of the ground of the test strip can be eliminated by obtaining the difference R-T or ratio R/T between the reflective intensity T of the test line and the reflective intensity R of the ground of the test strip. In such a case, the DET is obtained according to the following equation:

$$DET=R-T \text{ or}$$

$$DET=R/T$$

In the embodiments above-mentioned, the reflective intensity R of the ground is defined as (1) the peak value of the mountain portion between the valleys b and c, or (2) the center value or average value of the peak values of the respective mountain portions. Instead of such procedure, (R1–T) may be used instead of (R–T), and (R2–C) may be used instead of (R–C) wherein R1 is the reflective intensity of the ground in the immediate proximity of the test line 4b, and R2 is the reflective intensity of the ground in the immediate proximity of the control line 4a. In such a case, even though a test strip presents an uneven distribution of reflective intensity, an accurate judgment can be made.

In each of the test strip measuring methods above-mentioned, the reflective intensity of a test strip is checked, but transmission intensity may be checked. Further, when a test strip emits fluorescence, the fluorescence intensity may be checked.

The invention claimed is:

1. A method for measuring optical characteristics including reflective intensity, transmission intensity, or fluorescent intensity of a test strip that has been immersed in a liquid to be tested and is held by a test strip holder, comprising the steps of:

(a) moving a test strip holder having a test strip held thereon in a moving direction at a uniform rate, said test strip having a test line that appears on the test strip after it has been immersed in a liquid to be tested;

(b) detecting at a detection position of an optical system including a light receiving portion, optical characteristics of the test strip holder and the test strip during movement of the test strip holder and the test strip in the moving direction;

(c) measuring a period of time from a start of the movement of the test strip holder and the test strip to when a forefront end of the test strip in the moving direction is detected at the detection position based on the detected optical characteristics of the test strip holder and the test strip, wherein the period of time represents a distance between the forefront end of the test strip and said detection position at the start of this time measurement;

(d) determining a point of time when the test line on the test strip will be detected at the detection position after the test strip holder has started to move in the moving direction or determining a position where the test line on the test strip will be detected, based on the measured period of time obtained in step (c);

(e) obtaining a determinant using a difference or ratio between an optical characteristic of a background of the test strip where the test line does not appear and an optical characteristic of the test line when the test line on the test strip is detected at the determined point of time or in the determined position obtained in step (d); and (f) using the obtained determinant to conduct a quantitative measurement of the test line on the test strip.

2. A test strip measuring method according to claim 1, wherein in step (e), a judgment of negativity is made when the test line is not detected at the determined point of time or in the determined position.

3. A test strip measuring method according to claim 1, wherein in step (e), to identify the test line, the difference between the optical characteristic of a portion which is presumed to be the test line, and the optical characteristic of the background of the test strip, is compared with a test line threshold value, and the portion is identified as the test line when the difference is greater than the test line threshold value.

4. A test strip measuring method according to claim 1, wherein a plurality of test lines on the test strip are measured.

5. A test strip measuring method according to claim 1, wherein a concentration of the liquid to be tested is determined from the determinant using a calibration curve.

6. A test strip measuring method according to claim 1, comprising the further steps of:
(g) determining a point of time when a control line on the test strip will be detected at the detection position or determining a position where the control line will be detected, based on the measured period of time obtained in step (c); and
(h) obtaining a reference value for judging the determinant obtained in step (e), which reference value is a difference or ratio between the optical characteristic of the background of the test strip and an optical characteristic of the control line which was detected on the test strip at the determined point of time or in the determined position obtained in step (g).

7. A test strip measuring method according to claim 6, wherein in step (h), a judgment is made that the test strip is defective or the inspection is erroneous when the control line is not detected at the determined point of time or in the determined position.

8. A test strip measuring method according to claim 6, wherein after the control line has been detected, there is determined the point of time when the test line will be detected, or the determined position where the test line will be detected.

9. A test strip measuring method according to claim 6, wherein in step (h) to identify the control line, the difference between the optical characteristic of a portion which is presumed to be the control line, and the optical characteristic of the background of the test strip, is compared with a control line threshold value, and the portion is identified as the control line when the difference is greater than the control line threshold value.

10. A test strip measuring method according to claim 6, wherein a plurality of control lines on the test strip are measured.

11. A test strip measuring method for measuring optical characteristics including reflective intensity, transmission intensity, or fluorescent intensity of a test strip that has been immersed in a liquid to be tested and is held by a test strip holder, comprising the steps of:
(a) moving a test strip holder having a test strip held thereon in a moving direction at a uniform rate, said test strip having a test line that appears on the test strip after it has been immersed in a liquid to be tested in the moving direction;
(b) detecting at a detection position of an optical system including a light receiving portion, optical characteristics of the test strip holder and the test strip during movement of the test strip holder and the test strip in the moving direction;
(c) measuring a period of time from a start of the movement of the test strip holder and the test strip to when a forefront end of the test strip in the moving direction is detected at the detection position based on the detected optical characteristics of the test strip holder and the test strip, wherein the period of time represents a distance between the forefront end of the test strip and said detection position at the start of this time measurement;
(d) determining a point of time when the test line on the test strip will be detected at the detection position after the test strip holder has started to move in the moving direction or determining a position where the test line on the test strip will be detected, based on the measured period of time obtained in step (c);
(e) obtaining a determinant using a difference or ratio between an optical characteristic of a background of the test strip where the test line does not appear and an optical characteristic of the test line when the test line on the test strip is detected at the determined point of time or in the determined position obtained in step (d); and
(f) comparing the obtained determinant with a threshold value for qualitative judgment of the test line on the test strip.

12. A test strip measuring method according to claim 11, wherein in step (e), a judgment of negativity is made when the test line is not detected at the determined point of time or in the determined position.

13. A test strip measuring method according to claim 11, wherein in step (e) to identify the test line, the difference between the optical characteristic of a portion which is presumed to be the test line, and the optical characteristic of the background of the test strip, is compared with a second threshold value, and the portion is identified as the test line when the difference is greater than the second threshold value.

14. A test strip measuring method according to claim 11, comprising the further steps of:
(g) determining a point of time when a control line on the test strip will be detected at the detection position or determining a position where the control line will be detected, based on the measured period of time obtained in step (c); and
(h) obtaining a reference value for judging the determinant obtained in step (e), which reference value is a difference or ratio between the optical characteristic of the background of the test strip and an optical characteristic of the control line which was detected on the test strip at the determined point of time or in the determined position obtained in step (g).

15. A test strip measuring method according to claim 14, wherein in step h, a judgment is made that the test strip is defective or the inspection is erroneous when the control line is not detected at the determined point of time or in the determined position.

16. A test strip measuring method according to claim 14, wherein after the control line has been detected, there is determined the point of time when the test line will be detected or the determined position where the test line will be detected.

17. A test strip measuring method according to claim 14, wherein in step (h) to identify the control line, the difference between the optical characteristic of a portion which is presumed to be the control line, and the optical characteristic of the background of the test strip, is compared with a third threshold value, and the portion is identified as the control line when the difference is greater than the third threshold value.

* * * * *